(12) United States Patent
McCairn et al.

(10) Patent No.: US 8,337,720 B2
(45) Date of Patent: Dec. 25, 2012

(54) SEMICONDUCTOR NANOPARTICLE CAPPING AGENTS

(75) Inventors: Mark C. McCairn, Newent (GB); Steven M. Daniels, Manchester (GB); Siobhan Cummins, Ludlow (GB); Nigel Pickett, London (GB)

(73) Assignee: Nanoco Technologies, Ltd., Manchester (GB)

( * ) Notice: Subject to any disclaimer, the term of this patent is extended or adjusted under 35 U.S.C. 154(b) by 623 days.

(21) Appl. No.: 12/392,719

(22) Filed: Feb. 25, 2009

(65) Prior Publication Data

US 2009/0212258 A1    Aug. 27, 2009

Related U.S. Application Data

(60) Provisional application No. 61/031,218, filed on Feb. 25, 2008.

(51) Int. Cl.
*H01L 51/42* (2006.01)
(52) U.S. Cl. .......... 252/301.4 R; 252/301.6 S; 977/813; 977/773
(58) Field of Classification Search ........... 252/301.4 R, 252/301.6 S; 977/813, 773
See application file for complete search history.

(56) References Cited

U.S. PATENT DOCUMENTS

| 2,769,838 A | 11/1956 | Matter et al. |
| 3,524,771 A | 8/1970 | Green |
| 4,609,689 A | 9/1986 | Schwartz et al. |
| 6,114,038 A | 9/2000 | Castro et al. |
| 6,207,229 B1 | 3/2001 | Bawendi et al. |
| 6,221,602 B1 | 4/2001 | Barbera-Guillem et al. |
| 6,261,779 B1 | 7/2001 | Barbera-Guillem et al. |
| 6,322,901 B1 | 11/2001 | Bawendi et al. |
| 6,326,144 B1 | 12/2001 | Bawendi et al. |
| 6,333,110 B1 | 12/2001 | Barbera-Guillem et al. |
| 6,379,635 B2 | 4/2002 | O'Brien et al. |
| 6,423,551 B1 | 7/2002 | Weiss et al. |
| 6,426,513 B1 | 7/2002 | Bawendi et al. |
| 6,607,829 B1 | 8/2003 | Bawendi et al. |
| 6,660,379 B1 | 12/2003 | Lakowicz et al. |
| 6,699,723 B1 | 3/2004 | Weiss et al. |
| 6,815,064 B2 | 11/2004 | Treadway et al. |
| 6,855,551 B2 | 2/2005 | Bawendi et al. |
| 6,914,264 B2 | 7/2005 | Chen et al. |
| 6,992,202 B1 | 1/2006 | Banger et al. |
| 7,151,047 B2 | 12/2006 | Chan et al. |
| 7,235,361 B2 | 6/2007 | Bawendi et al. |
| 7,264,527 B2 | 9/2007 | Bawendi et al. |
| 7,544,725 B2 | 6/2009 | Pickett et al. |
| 7,588,828 B2 | 9/2009 | Mushtaq et al. |
| 7,674,844 B2 | 3/2010 | Pickett et al. |
| 7,803,423 B2 | 9/2010 | O'Brien et al. |
| 7,867,556 B2 | 1/2011 | Pickett |
| 7,867,557 B2 | 1/2011 | Pickett et al. |
| 2003/0017264 A1 | 1/2003 | Treadway et al. |
| 2003/0106488 A1 | 6/2003 | Huang et al. |
| 2003/0148024 A1 | 8/2003 | Kodas et al. |
| 2004/0007169 A1* | 1/2004 | Ohtsu et al. ............ 117/84 |
| 2004/0036130 A1 | 2/2004 | Lee et al. |
| 2004/0110002 A1 | 6/2004 | Kim et al. |
| 2004/0110347 A1 | 6/2004 | Yamashita |
| 2004/0178390 A1 | 9/2004 | Whiteford et al. |
| 2004/0250745 A1 | 12/2004 | Ogura et al. |
| 2005/0048010 A1* | 3/2005 | Kliss et al. ............ 424/59 |
| 2005/0098204 A1 | 5/2005 | Roscheisen et al. |
| 2005/0129947 A1 | 6/2005 | Peng et al. |
| 2005/0145853 A1 | 7/2005 | Sato et al. |
| 2006/0019098 A1 | 1/2006 | Chan et al. |
| 2006/0057382 A1 | 3/2006 | Treadway et al. |
| 2006/0061017 A1 | 3/2006 | Strouse et al. |
| 2006/0068154 A1 | 3/2006 | Parce et al. |
| 2006/0110279 A1 | 5/2006 | Han et al. |
| 2006/0118757 A1 | 6/2006 | Kilmov et al. |
| 2006/0130741 A1 | 6/2006 | Peng et al. |
| 2007/0012941 A1 | 1/2007 | Cheon |
| 2007/0034833 A1 | 2/2007 | Parce et al. |
| 2007/0059705 A1 | 3/2007 | Lu et al. |
| 2007/0104865 A1 | 5/2007 | Pickett |
| 2007/0110816 A1 | 5/2007 | Jun et al. |
| 2007/0114520 A1 | 5/2007 | Garditz et al. |
| 2007/0125983 A1 | 6/2007 | Treadway et al. |
| 2007/0131905 A1 | 6/2007 | Sato et al. |

(Continued)

FOREIGN PATENT DOCUMENTS

CN  1394599  2/2003

(Continued)

OTHER PUBLICATIONS

Barron, "Group III Materials: New Phases and Nono-particles with Applications in Electronics and Optoelectronics," Office of Naval Research Final Report (1999). Dabousi et al., "(CdSe)ZnS Core-Shell Quantum Dots: Synthesis and Characterization of a Size Series of Highly Luminescent Nanocrystallites," Jrl. Phys. Chem.,(1997) 101, pp. 9463-9475.
Dehnen et al., "Chalcogen-Bridged Copper Clusters," Eur. J. Inorg. Chem., (2002) pp. 279-317.
Eisenmann et al., "New Phosphido-bridged Multinuclear Complexes of Ag and Zn," Zeitschrift fur anorganische und allgemeine Chemi (1995). (1 page—abstract).

(Continued)

*Primary Examiner* — Carol M Koslow
(74) *Attorney, Agent, or Firm* — Wong, Cabello, Lutsch, Rutherford & Brucculeri, LLP

(57) ABSTRACT

Embodiments of the invention involve semiconductor nanoparticle capping ligands, their production and use. Ligands may have the formula

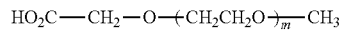

with m ranging from approximately 8 to approximately 45. An embodiment provides a method of forming a compound of the formula

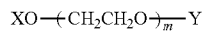

including the steps of providing a first starting material comprising poly(ethyleneglycol) and reacting the first starting material with a second starting material comprising a functional group for chelating to the surface of a nanoparticle to thereby form the compound.

13 Claims, 1 Drawing Sheet

U.S. PATENT DOCUMENTS

| | | | |
|---|---|---|---|
| 2007/0199109 A1 | 8/2007 | Yi et al. |
| 2007/0202333 A1 | 8/2007 | O'Brien et al. |
| 2007/0238126 A1 | 10/2007 | Pickett et al. |
| 2008/0107911 A1 | 5/2008 | Liu et al. |
| 2008/0112877 A1 | 5/2008 | Xiao et al. |
| 2008/0121844 A1 | 5/2008 | Jang et al. |
| 2008/0160306 A1 | 7/2008 | Mushtaq et al. |
| 2008/0220593 A1 | 9/2008 | Pickett et al. |
| 2008/0257201 A1 | 10/2008 | Harris et al. |
| 2008/0264479 A1 | 10/2008 | Harris et al. |
| 2009/0139574 A1 | 6/2009 | Pickett et al. |
| 2009/0212258 A1 | 8/2009 | Mccairn et al. |
| 2009/0263816 A1 | 10/2009 | Pickett et al. |
| 2010/0059721 A1 | 3/2010 | Pickett et al. |
| 2010/0068522 A1 | 3/2010 | Pickett et al. |
| 2010/0113813 A1 | 5/2010 | Pickett et al. |
| 2010/0123155 A1 | 5/2010 | Pickett et al. |
| 2010/0193767 A1 | 8/2010 | Naasani et al. |
| 2010/0212544 A1 | 8/2010 | Harris et al. |

FOREIGN PATENT DOCUMENTS

| | | | |
|---|---|---|---|
| EP | 1176646 | | 1/2002 |
| EP | 1783137 | | 5/2007 |
| EP | 1854792 | | 11/2007 |
| GB | 199518910.6 | | 9/1995 |
| GB | 2429838 | | 3/2007 |
| JP | 2002-121549 | * | 4/2002 |
| JP | 2005-139389 | | 6/2005 |
| JP | 2007-277130 | * | 10/2007 |
| WO | WO-97-10175 | | 3/1997 |
| WO | WO-02-04527 | | 1/2002 |
| WO | WO-0224623 | | 3/2002 |
| WO | WO-02-29140 | | 4/2002 |
| WO | WO-03-099708 | | 12/2003 |
| WO | WO-2004008550 | | 1/2004 |
| WO | WO-2004-033366 | | 4/2004 |
| WO | WO 2004/065362 | * | 8/2004 |
| WO | WO-2004-066361 | | 8/2004 |
| WO | WO-2004065362 | | 8/2004 |
| WO | WO-2005-021150 | | 3/2005 |
| WO | WO-2005-106082 | | 11/2005 |
| WO | WO-2005123575 | | 12/2005 |
| WO | WO-2006001848 | | 1/2006 |
| WO | WO-2006-017125 | | 2/2006 |
| WO | WO-2006075974 | | 7/2006 |
| WO | WO-2006-116337 | | 11/2006 |
| WO | WO-2006118543 | | 11/2006 |
| WO | WO-2006134599 | | 12/2006 |
| WO | WO-2007020416 | | 2/2007 |
| WO | WO-2007-049052 | | 5/2007 |
| WO | WO-2007-060591 | | 5/2007 |
| WO | WO-2007060591 | | 5/2007 |
| WO | WO-2007-065039 | | 6/2007 |
| WO | WO-2007098378 | | 8/2007 |
| WO | WO-2007102799 | | 9/2007 |
| WO | WO-2008013780 | | 1/2008 |
| WO | WO-2008054874 | | 5/2008 |
| WO | WO-2008133660 | | 11/2008 |
| WO | WO-2009016354 | | 2/2009 |
| WO | WO-2009040553 | | 4/2009 |
| WO | WO-2009106810 | | 9/2009 |

OTHER PUBLICATIONS

Müller et al., "From Giant Molecular Clusters and Precursors to Solid-state Structures," Current Opinion in Solid State and Materials Science, 4 (Apr. 1999) pp. 141-153.

Timoshkin, "Group 13 imido metallanes and their heavier analogs [RMYR']n (M=Al, Ga, In; Y=N, P, As, Sb)," Coordination Chemistry Reviews (2005).

Vittal, "The chemistry of inorganic and organometallic compounds with adameantane-like structures," Polyhedron, vol. 15, No. 10, pp. 1585-1642 (1996).

Zhong et al, "Composition-Tunable ZnxCu1-xSe Nanocrytals with High Luminescence and Stability", Jrl Amer. Chem. Soc. (2003).

International Search Report for PCT/GB2006/003028 mailed Jan. 22, 2007 (5 pages).

Nielsch et al., "Uniform Nickel Deposition into Ordered Alumina Pores by Pulsed Electrodeposition", Advanced Materials, 2000 vol. 12, No. 8, pp. 582-586.

Huang et al., "Bio-Inspired Fabrication of Antireflection Nanostructures by Replicating Fly Eyes", Nanotechnology (2008) vol. 19.

Xie et. al., "Synthesis and Characterization of Highly Luminescent CdSe-Core CdS/Zn0.5Cd0.5S/ZnS Multishell Nanocrystals," JACS Articles published on web Apr. 29, 2005.

Kim et. al., "Engineering InAsxP1-x/InP/ZnSe III-V Alloyed Core-Shell Quantum Dots for the Near-Infrared," JACS Articles published on web Jul. 8, 2005.

Rao et. al. "The Chemistry of Nanomaterials: Synthesis, Properties and Applications" (2004).

Trinidade et al., "Nanocrystalline Seminconductors: Synthesis, Properties, and Perspectives", Chemistry of Materials, (2001) vol. 13, No. 11, pp. 3843-3858.

International Search Report for PCT/GB2009/001928 mailed Dec. 8, 2009 (3 pagesq).

International Search Report for PCT/GB2009/002605 mailed Feb. 22, 2010 (3 pages).

Search Report for GB0813273.0 searched Dec. 8, 2008 (1 page).

Search Report for GB0814458.6 searched Dec. 5, 2008 (2 pages).

Search Report for GB0820101.4 searched Mar. 3, 2009 (1 page).

Search Report for GB0821122.9 searched Mar. 19, 2009 (2 pages).

Foneberov et al., "Photoluminescence of tetrahedral quantum-dot quantum wells" Physica E, 26:63-66 (2005).

Cao, "Effect of Layer Thickness on the Luminescence Properties of ZnS/CdS/ZnS quantum dot quantum well", J. of Colloid and Interface Science 284:516-520 (2005).

Harrison et al. "Wet Chemical Synthesis on Spectroscopic Study of CdHgTe Nanocrystals with Strong Near-Infrared Luminescence" Mat. Sci and Eng.B69-70:355-360 (2000).

Sheng et al. "In-Situ Encapsulation of Quantum Dots into Polymer Microsphers", Langmuir 22(8):3782-3790 (2006).

W. Peter Wuelfing et al., "Supporting Information for Nanometer Gold Clusters Protected by Surface Bound Monolayers of Thiolated Poly (ethylene glycol) Polymer Electrolyte" Journal of the American Chemical Society (XP002529160).

International Search Report for PCT/GB2009/000510 mailed Jul. 6, 2010 (16 pages).

International Search Report for PCT/GB2008/003958 mailed Sep. 4, 2009 (3 pages).

Banger et al., "Ternary single-source precursors for polycrystalline thin-film solar cells" Applied Organometallic Chemistry, 16:617-627, XP002525473 Scheme 1 Chemical Synthesis (2002).

D Qi, M Fischbein, M Drndic, S. Selmic, "Efficient polymer-nanocrystal quantum-dot photodetectors", Appl. Phys. Lett., 2004, 84, 4295.

Shen et al., "Photoacoustic and photoelectrochemical characterization of CdSe-sensitized Ti02 electrodes composed of nanotubes and nanowires" Thin Solid Films, Elsevier-Sequoia S.A. Lausanne, CH vol. 499, No. 1-2, Mar. 21, 2006, pp. 299-305, XP005272241 ISSN: 0040-6090.

Smestad GP, et al., "A technique to compare polythiophene solid-state dye sensitized Ti02 solar cells to liquid junction devices" Solar Energy Materials and Solar Cells, Elsevier Science Publishers, Amsterdam, NL, vol. 76, No. 1, Feb. 15, 2003, pp. 85-105, XP004400821 ISSN: 0927-0248.

Chen et al., "Electrochemically synthesized CdS nanoparticle-modified Ti02 nanotube-array photoelectrodes: Preparation, characterization, and application to photoelectrochemical cells" Journal of Photochemistry and Photobiology, a: Chemistry, Elsevier Sequoia Lausanne, CH, vol. 177, No. 2-3, Jan. 25, 2006, pp. 177-184, XP005239590 ISSN: 1010-6030.

Wang, et al., "In situ polymerization of amphiphilic diacetylene for hole transport in solid state dye-sensitized solar cells" Organic Electronics, El Sevier, Amsterdam NL, vol. 7, No. 6, Nov. 18, 2006, pp. 546-550, XP005773063 ISSN: 1566-1199.

International Search Report and Written Opinion for PCT/GB2008/001457 mailed Aug. 21, 2008 (14 pages).

Borchert et al., "High Resolution Photoemission STudy of CdSe and CdSe/ZnS Core-Shell Nanocrystals," Journal of Chemical Physics, vol. 119, No. 3, pp. 1800-1807 (2003).
Gaponik et al., "Thiol-Capping of CdTe Nanocrystals: An Alternative to Organometallic Synthetic Routes," Journal of Physical Chemistry B, vol. 106, No. 29, pp. 7177-7185 (2002).
Pickett et al., "Syntheses of Semiconductor Nanoparticles Using Single-Molecular Precursors," The Chemical Record, vol. 1 pp. 467-479 (2001).
Aldana, J. et al. "Photochemical Instability of CdSe Nanocrystals Coated by Hydrophilic Thiols", J. Am. Chem. Soc. (2001), 123: 8844-8850.
Alivisatos, A.P. "Perspectives on the Physical Chemistry of Semiconductor Nanocrystals", J. Phys. Chem., (1996), 100, pp. 13226-13239.
Battaglia et al., "Colloidal Two-dimensional Systems: CdSe Quantum Shells and Wells," Angew Chem. (2003) 115:5189.
Bawendi, M.G. The Quantum Mechanics of Larger Semiconductor Clusters ("Quantum Dots"), Annu. Rev. Phys. Chem. (1990), 42: 477-498.
Berry, C.R. "Structure and Optical Absorption of AgI Microcrystals", Phys. Rev. (1967) 161: 848-851.
Bunge, S.D. et al. "Growth and morphology of cadmium chalcogenides: the synthesis of nanorods, tetrapods, and spheres from CdO and Cd(O2CCH3)2", J. Mater. Chem. (2003) 13: 1705-1709.
Castro et al., "Synthesis and Characterization of Colloidal CuInS2 Nanoparticles from a Molecular Single-Source Precursors," J. Phys. Chem. B (2004) 108:12429.
Contreras et al., "ZnO/ZnS(O,OH)/Cu(In,Ga)Se2/Mo Solar Cell with 18:6% Efficiency," from 3d World Conf. on Photovol. Energy Conv., Late News Paper, (2003) pp. 570-573.
Cui et al., "Harvest of near infrared light in PbSe nanocrystal-polymer hybrid photovoltaic cells," Appl. Physics Lett. 88 (2006) 183111-183111-3.
Cumberland et al., "Inorganic Clusters as Single-Source Precursors for Preparation of CdSe, ZnSe, and CdSe/ZnS Nanomaterials" Chemistry of Materials, 14, pp. 1576-1584, (2002).
Daniels et al., "New Zinc and Cadmium Chalcogenide Structured Nanoparticles," Mat. Res. Soc. Symp. Proc. 789 (2004).
Eychmüller, A. et al. "A quantum dot quantum well: CdS/HgS/CdS", Chem. Phys. Lett. 208, pp. 59-62 (1993).
Fendler, J.H. et al. "The Colloid Chemical Approach to Nanostructured Materials", Adv. Mater. (1995) 7: 607-632.
Gao, M. et al. "Synthesis of PbS Nanoparticles in Polymer Matrices", J. Chem. Soc. Commun. (1994) pp. 2779-2780.
Gur et al., "Air stable all-inorganic nanocrystal solar cells processed from solution," Lawrence Berkeley Natl. Lab., Univ. of California, paper LBNL-58424 (2005).
Guzelian, A. et al. "Colloidal chemical synthesis and characterization of InAs nanocrystal quantum dots", Appl. Phys. Lett. (1996) 69: 1432-1434.
Hagfeldt, A. et al. "Light-induced Redox Reactions in Nanocrystalline Systems", Chem. Rev. (1995) 95: 49-68.
Henglein, A. "Small-Particle Research: Physicochemical Properties of Extremely Small Colloidal Metal and Semiconductor Particles", Chem Rev. (1989) 89: 1861-1873.
Hirpo et al., "Synthesis of Mixed Copper-Indium Chalcogenolates. Single-Source Precursors for the Photovoltaic Materials CuInQ2 (Q=S, Se)," J. Am. Chem. Soc. (1993) 115:1597.
International Search Report for PCT/GB2005/001611 mailed Sep. 8, 2005 (5 pages).
Jegier, J.A. et al. "Poly(imidogallane): Synthesis of a Crystalline 2-D Network Solid and Its Pyrolysis to Form Nanocrystalline Gallium Nitride in Supercritical Ammonia", Chem. Mater. (1998) 10: 2041-2043.
Kaelin et al., "CIS and CIGS layers from selenized nanoparticle precursors," Thin Solid Films 431-432 (2003) pp. 58-62.
Kapur et al., "Non-Vacuum processing of CuIn1-xGaxSe2 solar cells on rigid and flexible substrates using nanoparticle precursor inks," Thin Solid Films 431-432 (2003) pp. 53-57.
Kher, S. et al. "A Straightforward, New Method for the Synthesis of Nanocrystalline GaAs and GaP", Chem. Mater. (1994) 6: 2056-2062.

Law et al., "Nanowire dye-sensitized solar cells," Nature Mater. (2005) vol. 4 pp. 455-459.
Lieber, C. et al. "Understanding and Manipulating Inorganic Materials with Scanning Probe Microscopes", Angew. Chem. Int. Ed. Engl. (1996) 35: 687-704.
Little et al., "Formation of Quantum-dot quantum-well heteronanostructures with large lattice mismatch: Zn/CdS/ZnS," 114 J. Chem. Phys. 4 (2001).
LØver, T. et al. "Preparation of a novel CdS nanocluster material from a thiophenolate-capped CdS cluster by chemical removal of SPh ligands", J. Mater Chem. (1997) 7(4): 647-651.
Matijevic, E., "Monodispersed Colloids: Art and Science", Langmuir (1986) 2:12-20.
Matijevic, E. "Production of Mondispersed Colloidal Particles", Ann. Rev. Mater. Sci. (1985) 15: 483-518.
Mekis, I. et al., "One-Pot Synthesis of Highly Luminescent CdSe/CdS Core-Shell Nanocrystals via Organometallic and "Greener" Chemical Approaches", J. Phys. Chem. B. (2003) 107: 7454-7462.
Micic et al., "Synthesis and Characterization of InP, GaP, and GaInP$_2$ Quantum Dots", J. Phys. Chem. (1995) pp. 7754-7759.
Milliron et al., "Electroactive Surfactant Designed to Mediate Electron Transfer between CdSe Nanocrystals and Organic Semiconductors," Adv. Materials (2003) 15, No. 1, pp. 58-61.
Murray, C.B. et al., "Synthesis and Characterization of Nearly Monodisperse CdE (E=S, Se, Te) Semiconductor Nanocrystallites", J. Am. Chem. Soc. (1993) 115 (19) pp. 8706-8715.
Nazeeruddin et al., "Conversion of Light to Electricity by cis-X2Bis(2,2'bipyridyl-4,4'-dicarboxylate)ruthenium(II) Charge-Transfer Sensitizers (X= Cl-, Br-, I-, CN-, and SCN-) on Nanocrystalline TiO2 Electrodes," J. Am. Chem. Soc. (1993) 115:6382-6390.
Nazeeruddin et al., "Engineering of Efficient Panchromatic Sensitizers for Nanocrystalline TiO2-Based Solar Cells," J. Am. Chem. Soc. (2001) 123:1613-1624.
O'Brien et al., "The Growth of Indium Selenide Thin Films from a Novel Asymmetric Dialkydiselenocarbamate," 3 Chem. Vap. Depos. 4, pp. 227 (1979).
Olshaysky, M.A., et al. "Organometallic Synthesis of GaAs Crystallites Exhibiting Quantum Confinement", J. Am. Chem. Soc. (1990) 112: 9438-9439.
Patents Act 1977: Search Report under Section 17 for Application No. GB0409877.8 dated Oct. 7, 2004 (2 pages).
Patent Act 1977 Search Report under Section 17 for Application No. GB0522027.2 dated Jan. 27, 2006 (1 page).
Patent Act 1977 Search Report under Section 17 for Application No. GB0606845.6 dated Sep. 14, 2006.
Patent Act 1977 Search Report under Section 17 for Application No. GB0719073.9.
Patent Act 1977 Search Report under Section 17 for Application No. GB0719075.4.
Patent Act 1977 Search Report under Section 17 for Application No. GB0723539.3 dated Mar. 27, 2008 (1 page).
Peng et al., "Kinetics of I-VI and III-V Colloidal Semiconductor Nanocrystal Growth: "Focusing" os Size Distributions", J. Am. Chem. Soc., (1998) 129: 5343-5344.
Peng et al., "Mechanisms of the Shape Evolution of CdSe Nanocrystals", J. Am. Chem. Soc. (2001) 123:1389.
Peng et al., "Shape control of CdSe nanocrystals", Nature, (2000) vol. 404, No. 6773, pp. 59-61.
Pradhan, N. et al. "Single-Precursor, One-Pot Versatile Synthesis under near Ambient Conditions of Tunable, Single and Dual Band Flourescing Metal Sulfide Nanoparticles", J. Am. Chem. Soc. (2003) 125: 2050-2051.
Qi et al., "Efficient polymer-nanocrystal quantum-dot photodetectors," Appl. Physics Lett. 86 (2005) 093103-093103-3.
Qu, L. et al. "Alternative Routes toward High Quality CdSe Nanocrystals", Nano Lett. (2001) vol. 1, No. 6, pp. 333-337.
Robel et al., "Quantum Dot Solar Cells. Harvesting Light Energy with CdSe Nanocrystals Molecularly Linked to Mesoscopic TiO2 Films," J. Am. Chem. Soc. (2006) 128: 2385-2393.
Salata, O.V. et al. "Uniform GaAs quantum dots in a polymer matrix", Appl. Phys. Letters (1994) 65(2): 189-191.

Sercel, P.C. et al. "Nanometer-scale GaAs clusters from organometallic percursors", Appl. Phys. Letters (1992) 61: 696-698.

Steigerwald, M.L. et al. "Semiconductor Crystallites: A Class of Large Molecules", Acc. Chem. Res. (1990) 23: 183-188.

Stroscio, J.A. et al. "Atomic and Molecular Manipulation with the Scanning Tunneling Microscope", Science (1991), 254: 1319-1326.

Trinidade et al., "A Single Source Spproach to the Synthesis of CdSe Nanocrystallites", Advanced Materials, (1996) vol. 8, No. 2, pp. 161-163.

Vayssieres et al., "Highly Ordered SnO2 Nanorod Arrays from Controlled Aqueous Growth," Angew. Chem. Int. Ed. (2004) 43: 3666-3670.

Wang Y. et al. "PbS in polymers, From molecules to bulk solids", J. Chem. Phys. (1987) 87: 7315-7322.

Weller, H. "Colloidal Semiconductor Q-Particles: Chemistry in the Transition Region Between Solid State and Molecules", Angew. Chem. Int. Ed. Engl. (1993) 32: 41-53.

Weller, H. "Quantized Semiconductor Particles: A Novel State of Mater for Materials Science", Adv. Mater. (1993) 5: 88-95.

Wells, R.L. et al. "Synthesis of Nanocrystalline Indium Arsenide and Indium Phosphide from Indium(III) Halides and Tris (trimethylsilyl)pnicogens. Synthesis, Characterization, and Decomposition Behavior of I3In-P(SiMe3)3", Chem. Mater. (1995) 7: 793-800.

Yu et al., "Polymer Photovoltaic Cells: Enhanced Efficiencies via a Network of Internal Donor-Acceptor Heterojunctions," 270 Science 5243 (1995), pp. 1789-1791.

* cited by examiner

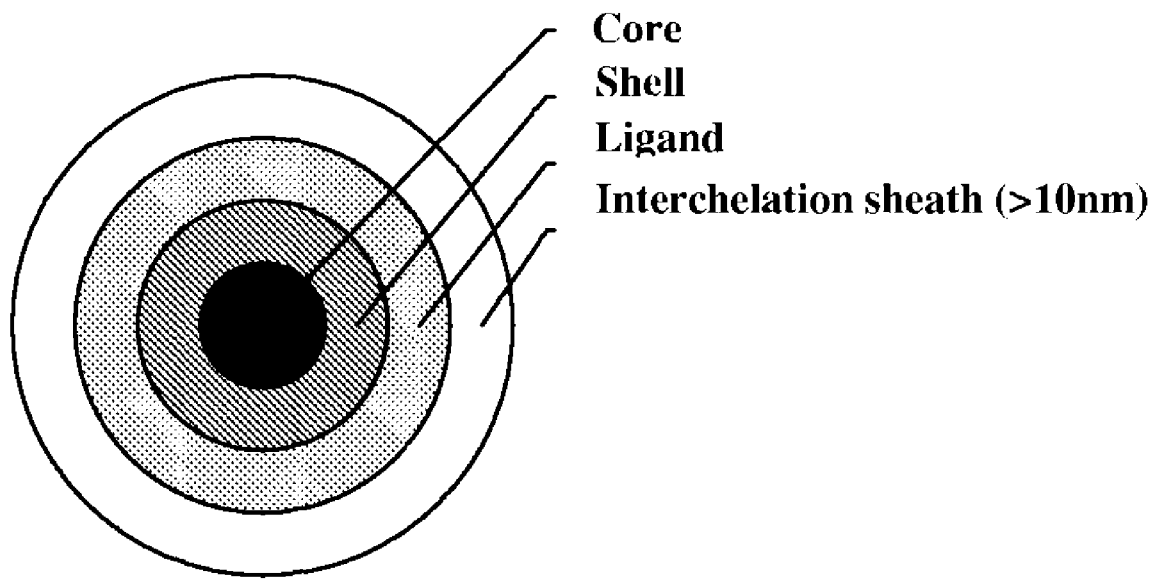

SEMICONDUCTOR NANOPARTICLE CAPPING AGENTS

CROSS-REFERENCE TO RELATED APPLICATION

This application claims the benefit of and priority to co-pending U.S. Provisional Patent Application No. 61/031,218, filed Feb. 25, 2008, the entire contents of which are herein incorporated by reference.

FIELD OF THE INVENTION

This invention relates to semiconductor nanoparticle capping ligands, their production and their use in preparing functionalized semiconductor nanoparticles.

BACKGROUND

The size of a semiconductor nanoparticle helps determine the electronic properties of the material; the bandgap energy may be inversely proportional to the size of the semiconductor nanoparticle as a consequence of quantum confinement effects. In addition, the large surface area to volume ratio of the nanoparticle affects the physical and chemical properties of the nanoparticle.

Single-core nanoparticles that include a single semiconductor material typically have relatively low quantum efficiencies. These low quantum efficiencies arise from non-radiative electron-hole recombinations that occur at defects and dangling bonds at the surface of the nanoparticle.

Core-shell nanoparticles typically include a single semiconductor core material that has a shell of a second semiconductor material grown epitaxially on the surface of the core. The shell material usually has a wider bandgap and similar lattice dimensions to the core semiconductor material. The intention of adding the shell may be to eliminate defects and dangling bonds from the surface of the core, and thereby confine charge carriers within the core and away from surface states that may function as centers for non-radiative recombination.

Still, the surfaces of core, core-shell, and core-multishell nanoparticles may have highly reactive dangling bonds. These may be passivated by capping the surface atoms with organic ligand molecules that inhibit aggregation of particles, protect the particle from its surrounding chemical environment, and (at least in the case of core nanoparticles) provide electronic stabilization. The capping ligand compound may be the solvent that is employed in the core growth and/or shelling of the nanoparticles. Alternatively, the capping ligand may be dissolved in an inert solvent and then used in the core growth and/or shelling of the nanoparticles. Either way, the ligand compound caps the surface of the nanoparticle by donating lone-pair electrons to the surface metal atoms of the nanoparticle.

Nanoparticles may typically be synthesized in the presence of a lipophilic ligand compound, resulting in nanoparticles that may be soluble in non-polar media. To decrease or eliminate this solubility, the ligand compound may be exchanged for a different ligand compound of greater polarity; however, the quantum yield of the nanoparticles diminishes as a result.

The resulting semiconductor nanoparticles may be used in a range of different applications, in which the nanoparticles may be externally excited by photo-excitation, electro-excitation, or another form of excitation, leading to electron-hole recombination and subsequent emission of photons in the form of light of a predetermined wavelength, e.g., visible light. The use of surface functionalized nanoparticles in such applications has so far, however, been limited by the loss in quantum yield upon surface functionalization.

SUMMARY

Disclosed herein are methods that may obviate or mitigate one or more of the above problems with current methods for producing surface functionalized semiconductor nanoparticles.

Some embodiments provide for the fabrication of capping ligands for semiconductor nanoparticles as well as the precursors of the capping ligands. The capping ligands disclosed herein may be utilized in and during the synthesis of the nanoparticles, resulting in nanoparticles of high quantum yield and polarity. The resulting semiconductor nanoparticles may be used in a range of different applications, such as display applications whereby the semiconductor nanoparticles may be incorporated into a device or transparent material; or incorporation into polar solvents (e.g., water and water-based solvents). The resulting nanoparticles may also be incorporated into inks, polymers or glasses; or attached to cells, biomolecules, metals, molecules and the like. The compounds and methods disclosed herein thus overcome the problems with prior art methods for the surface functionalization of semiconductor nanoparticles which have previously hindered the use of surface functionalized nanoparticles in such applications.

In an aspect, an embodiment of the invention includes a ligand having the formula

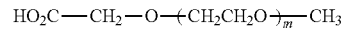

$$HO_2C-CH_2-O-(CH_2CH_2O)_{\overline{m}}-CH_3$$

with m ranging from 8 to 45.

One or more of the following features may be included. The ligand may be proximate a core or a shell of a nanoparticle. The core of the nanoparticle may have at least one semiconductor material. The ligand may be disposed within a solvent having at least one nanoparticle precursor material.

In another aspect, an embodiment of the invention includes a method of forming a compound of the formula

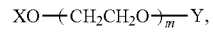

$$XO-(CH_2CH_2O)_{\overline{m}}-Y,$$

where X is an atom or chemical group, Y is an atom or chemical group and m is an integer. A first starting material including poly(ethyleneglycol) is provided, and the first starting material is reacted with a second starting material having a functional group for chelating to the surface of a nanoparticle, thereby forming the compound.

One or more of the following features may be included. The first starting material has a terminal hydroxyl group, the second starting material has a leaving group, and reacting the first and second starting materials includes detaching the leaving group. At least one nanoparticle may be capped with the compound. Variable X may be selected from H, $CH_3$, and $-CH_2CO_2H$. Variable Y may be selected from p-toluene sulphonate, carboxyl, $-CH_2CO_2H$, $PhCO_2H$, $SiPh_2{}^tBu$, phenyl, $-CH_2Ph$, thiol, amino, dithiocarbamato, phosphonic acid, phosphinic acid, vinyl, acetylene, aryl, and heteroaryl. Variable m may range from 8 to 45. At least one nanoparticle may include at least one semiconductor material.

In another aspect, an embodiment of the invention includes a method for producing capped nanoparticles including capping at least one nanoparticle with a compound of formula

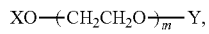

where X is an atom or chemical group, Y is an atom or chemical group and m is an integer.

In yet another aspect, embodiments of the invention include nanoparticles capped with a compound of formula

where X is an atom or chemical group, Y is an atom or chemical group and m is an integer.

One or more of the following features may be included. Variable X may be H, $CH_3$, and/or $-CH_2CO_2H$. Variable Y may be selected from p-toluene sulphonate, carboxyl, $-CH_2CO_2H$, $-PhCO_2H$, $-SiPh_2{}^tBu$, phenyl, $-CH_2Ph$, thiol, amino, dithiocarbamato, phosphonic acid, phosphinic acid, vinyl, acetylene, aryl, and/or heteroaryl. Variable m may range from 8 to 45. At least one nanoparticle may include at least one semiconductor material.

In another aspect, an embodiment of the invention includes a display device having a plurality of nanoparticles, each capped with a ligand having the formula

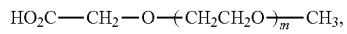

where m is an integer, disposed within a material substantially transparent to light.

One or more of the following features may be included. The display device may include means for exciting the plurality of nanoparticles such that the nanoparticles can emit visible light. Each of the plurality of nanoparticles may have a core including a first semiconductor material and a shell including a second semiconductor material different from the first semiconductor material.

BRIEF DESCRIPTION OF THE FIGURE

FIG. 1 schematically illustrates a quantum dot nanoparticle.

DETAILED DESCRIPTION

One embodiment provides for the preparation and use of a compound of the following formula in the production and capping of quantum dot nanoparticles:

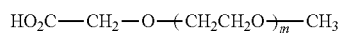

where m may be between 0 and approximately 4500, such as between 0 and approximately 450, or even such as 0 and approximately 17. In some embodiments, m may be approximately 8, approximately 13, approximately 17, or approximately 45. These compounds may be suitable for use as a ligand compound (i.e., a capping agent) for core growth and/or shelling of quantum dot nanoparticles.

One embodiment provides a ligand having the formula

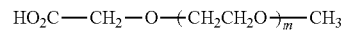

with m ranging from approximately 8 to approximately 45.

In one embodiment, the ligand is disposed proximate a core of a nanoparticle, where the core may include at least one semiconductor material. In a further embodiment, the ligand is disposed proximate a shell of a nanoparticle, the shell optionally including at least one semiconductor material. The ligand may be disposed within a solvent, in which case the solvent may further include at least one nanoparticle precursor material.

One embodiment of the invention relates to methods of synthesizing a compound of formula:

where m may be as defined above, X is selected from the group consisting of H, $-CH_3$, and $-CH_2CO_2H$, and Y is selected from the group consisting of p-toluene sulphonate, carboxyl (e.g. $-CH_2CO_2H$ or $PhCO_2H$), $SiPh_2{}^tBu$, phenyl (e.g., $-CH_2Ph$), thiol, amino, dithiocarbamato, phosphonic acid, phosphinic acid, vinyl, acetylene, aryl, heteroaryl, and the like.

Another embodiment provides for a method of forming a compound of the formula

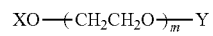

where the method includes the steps of providing a first starting material including poly(ethyleneglycol), and reacting the first starting material with a second starting material that includes a functional group for chelating to the surface of a nanoparticle, thereby forming the compound.

The first starting material may include a terminal hydroxyl group, the second starting material may include a leaving group, and the step of reacting the first and second starting materials may include detaching the leaving group.

In another embodiment, the method further includes capping at least one nanoparticle with the compound. Accordingly, another embodiment relates to a method for producing capped nanoparticles including carrying out the method described above and then capping at least one nanoparticle with the resulting compound of formula

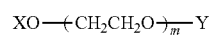

as defined above. Moreover, a further embodiment provides nanoparticles capped with a compound of formula

as defined above.

In another embodiment, the invention relates to a display device including a plurality of nanoparticles, each capped with a ligand having the formula

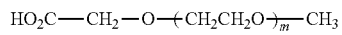

disposed within a material substantially transparent to light. The display device may include means for exciting the plurality of nanoparticles such that the nanoparticles emit visible light. Moreover, each of the plurality of nanoparticles may include a core including a first semiconductor material, and a shell including a second semiconductor material different from the first semiconductor material.

The above defined methods may include the steps of coupling, to an appropriately functionalized molecule of the formula X—W, the hydroxyl functionality of a poly(ethyleneglycol) starting material having the formula:

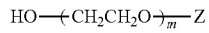

where m is as defined above, and Z is selected from the group consisting of H or —$CH_3$. X is selected from the group consisting of a leaving group such as a halogen, p-toluene sulphonate, mesyl ($CH_3$—$S(O)_2$—O—) or a nucleophile such as OH, and W is a suitable functional group to chelate to the surface of a nanoparticle, such as a carboxyl or thio group.

Z may be pre-functionalized to include a head group to afford the desired solubility to nanoparticles capped with the ligand produced as a result of the reaction of X—W with

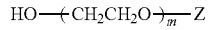

or Z may be subject to post-reaction modification so that it incorporates the desired head group, such as, but not limited to p-toluene sulphonate, carboxyl (e.g. —$CH_2CO_2H$ or -Ph$CO_2H$), SiPh$_2^t$Bu, phenyl (e.g. —$CH_2$Ph), thiol, amino, dithiocarbamato, phosphonic acid, phosphinic acid, vinyl, acetylene, aryl, heteroaryl, and the like.

In one embodiment, the ligand has the formula:

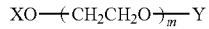

where X is —$CH_3$ and m is approximately 8 in both the poly(ethyleneglycol) methyl ether (~350) starting material and ligand compound. Y is H in the poly(ethyleneglycol) methyl ether (having a molecular weight of approximately 350) starting material and Y is —$CH_2CO_2H$ in the ligand compound.

Further embodiments provide semiconductor quantum dot nanoparticles incorporating the capping ligands defined above and methods for producing the same employing standard synthetic methods for binding such ligands to the nanoparticle surface.

The semiconductor material included in the nanoparticles capped with the above-defined capping ligands may incorporate ions from any one or more of groups 2 to 16 of the periodic table, including binary, ternary and quaternary materials, that is, materials incorporating two, three or four different ions respectively. By way of example, the nanoparticles may incorporate a core semiconductor material, such as, but not limited to, CdS, CdSe, CdTe, ZnS, ZnSe, ZnTe, InP, InAs, InSb, AlP, $Al_2S_3$, AlAs, AlSb, GaN, GaP, GaAs, GaSb, PbS, PbSe, Si, Ge and combinations thereof. Nanoparticles may possess cores with mean diameters of less than around 20 nm, such as less than around 15 nm and further such as in the range of around 2 nm to around 5 nm.

As mentioned above, in order to at least partially address issues related to non-radiative electron-hole recombinations that occur at defects and dangling bonds at the nanoparticle surface resulting in undesirably low quantum efficiencies, nanoparticle cores may be at least partially coated with one or more layers (also referred to herein as "shells") of a different material to the core, for example, a semiconductor material. Thus, the nanoparticles capped using ligands disclosed herein may incorporate one or more shell layers. The material included in the or each shell may incorporate ions from any one or more of groups 2 to 16 of the periodic table. Where a nanoparticle includes two or more shells, each shell may be formed of a different material. In an exemplary core/shell material, the core may be formed from one of the materials specified above and the shell may include a semiconductor material of larger band-gap energy and similar lattice dimensions to the core material. Example shell materials include, but are not limited to, ZnS, MgS, MgSe, MgTe and GaN. The confinement of charge carriers within the core and away from surface states provides quantum dots of greater stability and higher quantum yield. It will be appreciated that where two materials may be provided in adjacent layers of a semiconductor nanoparticle whose lattice structures do not correspond closely, it may be appropriate to ease any lattice strain that exists at the interface of the two materials by introducing a graded layer in between the two layers of material. The graded layer will typically include most, if not all, of the ions in each of the two adjacent layers but the proportions of the ions will vary from the core to the shell. The region of the graded layer adjacent to the core will include a majority of at least one of the ions in the core material, and the region of the graded layer adjacent to the shell will include a majority of the at least one of the ions in the shell material.

The mean diameter of quantum dot nanoparticles, which may be capped using the ligands disclosed herein, may be varied to modify the emission wavelength. The energy levels and hence the frequency of the quantum-dot fluorescence emission may be controlled by the material from which the quantum dot is made and the size of the quantum dot. Generally, quantum dots made of the same material have a more pronounced red emission the larger the quantum dot. In some embodiments, the quantum dots have diameters of around 1 nm to around 15 nm, such as around 1 nm to around 10 nm. The quantum dots preferably emit light having a wavelength of around 400 nm to around 900 nm, such as around 400 nm to around 700 nm.

Typically, as a result of the core and/or shelling procedures employed to produce the core, core/shell or core/multishell nanoparticles, the nanoparticles are at least partially coated with a surface binding ligand, such as myristic acid, hexadecylamine and/or trioctylphosphineoxide. Such ligands may typically be derived from the solvent in which the core and/or shelling procedures were carried out. While ligands of this type may increase the stability of the nanoparticles in non-polar media, provide electronic stabilization and/or negate undesirable nanoparticle agglomeration, as mentioned previously, such ligands usually prevent the nanoparticles from stably dispersing or dissolving in more polar media, such as aqueous solvents.

In some embodiments, quantum dots may be included that are aqueous-compatible, stable, small and of high quantum yield (see FIG. 1). Where lipophilic surface binding ligand(s) are coordinated to the surface of the quantum dots as a result of the core and/or shelling procedures (examples include hexadecylamine, trioctylphosphineoxide, myristic acid), such ligands may be exchanged entirely or partially with ligands disclosed herein using standard methods known to the skilled person, or the ligands disclosed herein may interchelate with the existing lipophilic surface binding ligands, again using standard methods.

Embodiments of the invention will now be illustrated by the following examples, which are given for the purpose of illustration only and without any intention of limiting the scope of the present invention.

EXAMPLES

Glassware was dried (120° C.) in an oven overnight. Dichloromethane ("DCM") and triethylamine ("TEA") were distilled from calcium hydride after heating at reflux for at least 1 hour. Tetrahydrofuran was distilled from Na/benzophenone after heating at reflux for at least 1 hour. Poly (ethylene glycols) were heated at 120° C. under high vacuum for 1 hour. All other reagents were used as received from a commercial supplier. All reaction mixtures were stirred magnetically and conducted under an atmosphere of dinitrogen gas.

Example 1

Synthesis of monomethyl ether poly(oxyethylene qlycol)$_{350}$ phthalimide

A. Synthesis of poly(oxyethylene glycol)$_{350}$ monomethyl ether p-toluene sulfonate Scheme 1: Synthesis of Poly(oxyethylene glycol)$_{350}$ monomethyl ether p-toluene sulfonate

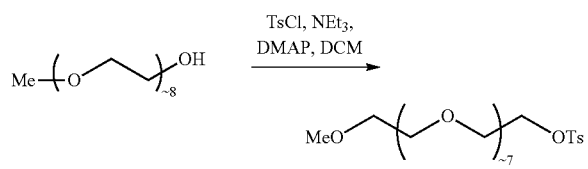

A solution of TsCl (27.792 g, 143.00 mmol) in DCM (80 mL) was added drop-wise over 2 hours to an ice-cooled solution of poly(oxyethylene glycol)$_{350}$ monomethyl ether (50.000 g, 143.00 mmol), triethylamine (40.30 mL, 290.0 mmol), and DMAP (0.177 g, 1.4 mmol) in DCM (75 mL), and the resultant mixture was left to stir overnight while warming to room temperature. The reaction mixture was washed with distilled water (2×200 mL), saturated sodium bicarbonate solution (2×100 mL), saturated citric acid solution (2×100 mL), dried over anhydrous sodium sulphate, filtered and concentrated under reduced pressure to give a yellow-colored oil. This oil was dissolved in hexane (3×200 mL) and the unreacted TsCl was separated from the reaction mixture by filtration. The filtrate was concentrated under reduced pressure to provide poly(oxyethylene glycol)$_{350}$ monomethyl ether p-toluene sulfonate as a pale yellow-colored oil.

B. Synthesis of monomethyl ether poly(oxyethylene glycol)$_{350}$ phthalimide

Scheme 2: Synthesis of monomethyl ether poly(oxyethylene glycol)$_{350}$ phthalimide

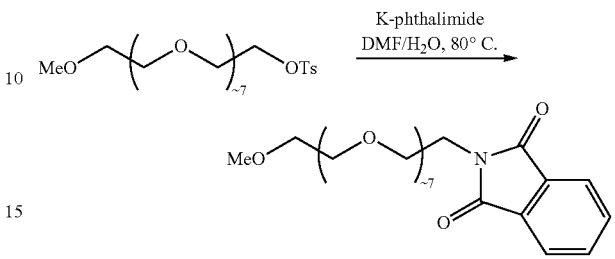

Potassium phthalimide (2.679 g, 14.48 mmol) was added to a solution of poly(oxyethylene glycol)$_{350}$ monomethyl ether p-toluene sulfonate (5.000 g, 9.65 mmol) in DMF (45 mL)/water (6 mL) and then stirred overnight (80° C.).

The reaction mixture was allowed to cool to room temperature, dissolved in DCM (100 mL) and washed sequentially with distilled water (6×500 mL), saturated brine (6×500 mL) (to remove DMF), distilled water (500 mL), then dried over anhydrous magnesium sulphate, filtered and concentrated under reduced pressure. The resultant oil was dissolved in the minimum volume of DCM, filtered, and then concentrated under reduced pressure to give monomethyl ether poly(oxyethylene glycol)$_{350}$ phthalimide.

The phthalimide group of the monomethyl ether poly(oxyethylene glycol)$_{350}$ phthalimide compound is an example of a terminal functional group that may be conveniently converted into another group (such as an amino group, e.g. —NH$_2$, when treated with a base) to confer to the resulting ligand the ability to bind to the surface of nanoparticles and/or the ability to modify the solubility of nanoparticles to which the ligand is bound.

Example 2

Synthesis of poly(oxyethylene glycol)$_{350}$ monomethyl ether acetic acid

A solution of bromoacetic acid (162.83 g, 1.1719 moles) in tetrahydrofuran (500 mL) was added dropwise to a suspension of sodium hydride (93.744 g, 2.3436 moles) in tetrahydrofuran (500 mL) that was stirred and cooled (0° C.). Poly (oxyethylene glycol)$_{350}$ monomethyl ether that had previously been dried (120° C., high vacuum, 1 hour) was dissolved in tetrahydrofuran (150 mL) and added dropwise to the reaction mixture. The reaction mixture was stirred while warming to room temperature overnight.

The reaction mixture was poured over ice, acidified (pH=1) and then concentrated under reduced pressure to give a white solid suspended in a yellow-colored oil. The oil was dissolved in CH$_2$Cl$_2$ (2.5 L) and the white solid was separated by filtration. The filtrate was washed with saturated NaHCO$_3$ (5×50 mL) and then concentrated under reduced pressure to give a yellow-colored oil. The oil was dissolved in water (2 L) and washed with diethyl ether (5×50 mL). The aqueous phase (pH of approximately 3) was acidified with 1M HCl$_{(aq)}$ to pH of approximately 1 and washed with diethyl ether (50 mL). The aqueous phase was concentrated under reduced pressure to give a colorless oil (298.78 g).

Example 3

Capping of Quantum Dots

Representative quantum-dot materials compatible with embodiments disclosed herein include CdSe, GaAs, InAs, InP, CuInS$_2$, CuInSe$_2$, and CuIn$_{1-x}$Ga$_x$Se$_2$. Nanoparticle synthesis may be carried out using techniques described, for example, in U.S. Pat. No. 6,379,635 and co-pending U.S. patent application Ser. Nos. 11/579,050 and 11/588,880. The nanoparticles may be characterized by any conventional technique (e.g., XRD, UV/Vis/Near-IR spectrometry, SEM, TEM, EDAX, photoluminescence spectrometry, elemental analysis).

QDs may be capped with the ligands described above (e.g. poly(oxyethylene glycol)$_{350}$ monomethyl ether acetic acid) using any one of a number of suitable methods known to the skilled person, which may optionally include ligand exchange and/or ligand interchelation methodologies.

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for producing capped nanoparticles comprising capping at least one nanoparticle with a compound of formula XO—(CH$_2$CH$_2$O)$_m$—Y, wherein X is selected from the group consisting of H, CH$_3$, and —CH$_2$CO$_2$H, Y is selected from the group consisting of p-toluene sulphonate, carboxyl, —CH$_2$CO$_2$H, -PhCO$_2$H, —SiPh$_2$$^t$Bu, phenyl, —CH$_2$Ph and phthalamide, and m is an integer, and wherein the capping comprises exchanging at least some existing ligands coating the nanoparticle for the compound of formula XO—(CH$_2$CH$_2$)$_m$—Y.

2. The method of claim 1, wherein m ranges from 8 to 45.

3. The method of claim 1, wherein the at least one nanoparticle comprises at least one semiconductor material.

4. The method of claim 3, wherein the semiconductor material is selected from one or more of the group of semiconductor materials consisting of CdS, CdSe, CdTe, ZnS, ZnSe, ZnTe, InP, InAs, InSb, AlP, Al$_2$S$_3$, AlAs, AlSb, GaN, GaP, GaAs, GaSb, PbS, PbSe, Si, and Ge.

5. The method of claim 1, wherein the existing ligands are lipophilic surface binding ligands.

6. The method of claim 1, wherein the existing ligands are selected from the group consisting of myristic acid, hexadecylamine and trioctylphosphineoxide.

7. The method of claim 1, wherein the capping increases the stability of the nanoparticle in aqueous media.

8. A method for producing capped nanoparticles comprising capping at least one nanoparticle with a compound of formula XO—(CH$_2$CH$_2$O)$_m$—Y wherein X is selected from the group consisting of H, CH$_3$, and —CH$_2$CO$_2$H, Y is selected from the group consisting of p-toluene sulphonate, carboxyl, —CH$_2$CO$_2$H, -PhCO$_2$H, —SiPh$_2$$^t$Bu, phenyl, —CH$_2$Ph and phthalamide, and m is an integer, wherein capping comprises interchelating the compound of formula XO—(CH$_2$CH$_2$O)$_m$—Y into existing ligands coating the nanoparticle.

9. The method of claim 8, wherein the existing ligands are lipophilic surface binding ligands.

10. The method of claim 8, wherein the existing ligands are selected from the group consisting of myristic acid, hexadecylamine and trioctylphosphineoxide.

11. A method of producing capped nanoparticles, the method comprising: forming a compound of the formula

XO—(CH$_2$CH$_2$O)$_m$—Y wherein X is selected from the group consisting of H, CH$_3$, and —CH$_2$CO$_2$H, Y is selected from the group consisting of p-toluene sulphonate, carboxyl, —CH$_2$CO$_2$H, -PhCO$_2$H, —SiPh$_2$$^t$Bu, phenyl, —CH$_2$Ph and phthalamide and m is an integer, by:

providing a first starting material comprising poly(ethyleneglycol) and a terminal hydroxyl group;

reacting the first starting material with a second starting material comprising a leaving group and a functional group for chelating to the surface of a nanoparticle thereby detaching the leaving group and forming the compound; and capping at least one nanoparticle with a compound of formula XO—(CH$_2$CH$_2$O)$_m$—Y.

12. The method of claim 11, wherein the leaving group is p-toluene sulfonate.

13. Nanoparticles capped with a compound of formula

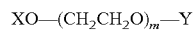

XO—(CH$_2$CH$_2$O)$_m$—Y wherein X is selected from the group consisting of H, CH$_3$, and —CH$_2$CO$_2$H, Y is selected from the group consisting of p-toluene sulphonate, carboxyl, —CH$_2$CO$_2$H, -PhCO$_2$H, —SiPh$_2$$^t$Bu, phenyl, —CH$_2$Ph and phthalamide and m is an integer, and wherein at least one of the nanoparticles comprises a semiconductor material selected from one or more of the group of semiconductor materials consisting of CdS, CdSe, CdTe, ZnS, ZnSe, ZnTe, InP, InAs, InSb, AlP, Al$_2$S$_3$, AlAs, AlSb, GaN, GaP, GaAs, GaSb, PbS, PbSe, Si, and Ge.

* * * * *